US00PP36047P2

(12) United States Plant Patent
Van Swieten

(10) Patent No.: US PP36,047 P2
(45) Date of Patent: Jul. 30, 2024

(54) ***PHALAENOPSIS* ORCHID PLANT NAMED 'PHA474649'**

(50) Latin Name: ***Phalaenopsis* hybrid**
Varietal Denomination: PHA474649

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,753

(22) Filed: Jan. 17, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP32,595 P2 * 12/2020 Van Swieten ..... A01H 6/62
Plt./311

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHA474649', particularly characterized by having numerous large, light greenish-yellow flowers with red-purple lips, leaf attitude is semi-erect, and is propagated by meristem tissue culture, is disclosed.

3 Drawing Sheets

Genus and species: *Phalaenopsis* hybrid.
Variety denomination: 'PHA474649'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA474649'.

The new *Phalaenopsis* plant is a product of a planned breeding program conducted by the inventor in Bleiswijk, the Netherlands. The objective of this breeding program was to create a new *Phalaenopsis* plant with large, light greenish-yellow flowers with red-purple lips suitable for potted plant production.

The new *Phalaenopsis* plant 'PHA474649' is a result of cross-pollination made by the inventor in April 2017 in Bleiswijk, the Netherlands, of the proprietary female, or seed parent, *Phalaenopsis* hybrid '13-57810-02' (unpatented) with the proprietary male, or pollen parent, *Phalaenopsis* hybrid '14-65219-03' (unpatented).

The new *Phalaenopsis* was selected by the inventor as a single plant within the progeny of the stated cross-pollination in a controlled greenhouse in Bleiswijk, the Netherlands, in March 2017. Asexual reproduction of the new *Phalaenopsis* plant by meristem tissue culture since 2018 in Bleiswijk, the Netherlands, has demonstrated that the new variety reproduces true to type with all the characteristics, as herein described, firmly fixed and retained through successive generations.

Community Plant Variety Rights for this variety have been applied for in the European Union on Apr. 19, 2023 (Application no. 2023/0886), by Applicant who obtained the subject matter disclosed directly from the inventor. 'PHA474649' has not been made publicly available or sold anywhere in the world prior to the effective filing date of this application with the exception of sales or disclosures made one year or less before the effective filing date of this claimed invention by Applicant who obtained 'PHA474649' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA474649' as a new and distinct variety of *Phalaenopsis* plant:

1) large, light greenish-yellow flowers with red-purple lips;
2) flower shape in lateral view is flat; and
3) leaf attitude is semi-erect.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2023. Colors in the photographs may differ from the color values cited in the detailed botanical description, which accurately describe the actual colors of the new variety.

DESCRIPTION OF THE NEW VARIETY

Figure 1:
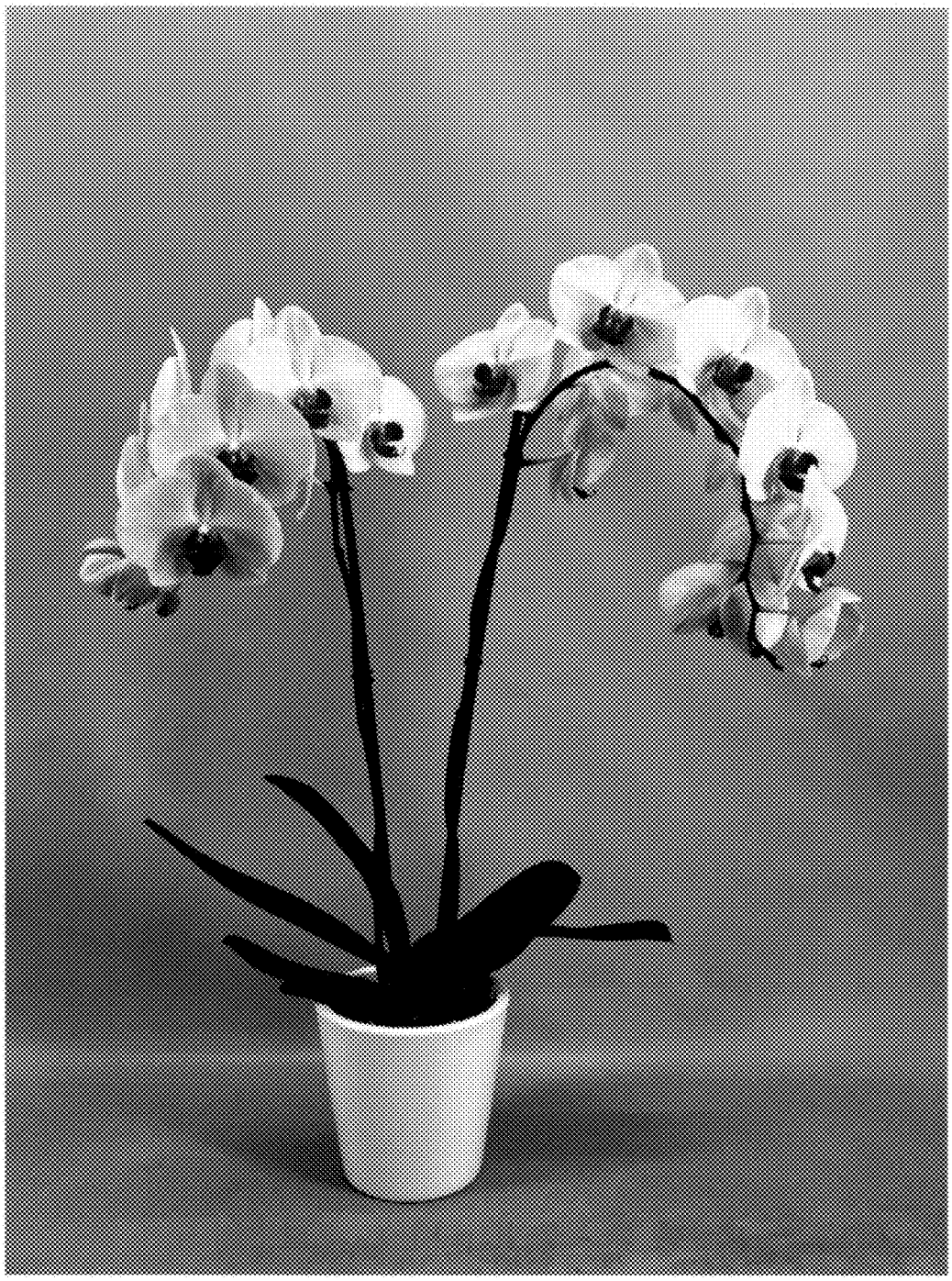
FIG. 1 shows the overall plant habit, including blooms, buds, and foliage of 'PHA474649'.
Figure 2:
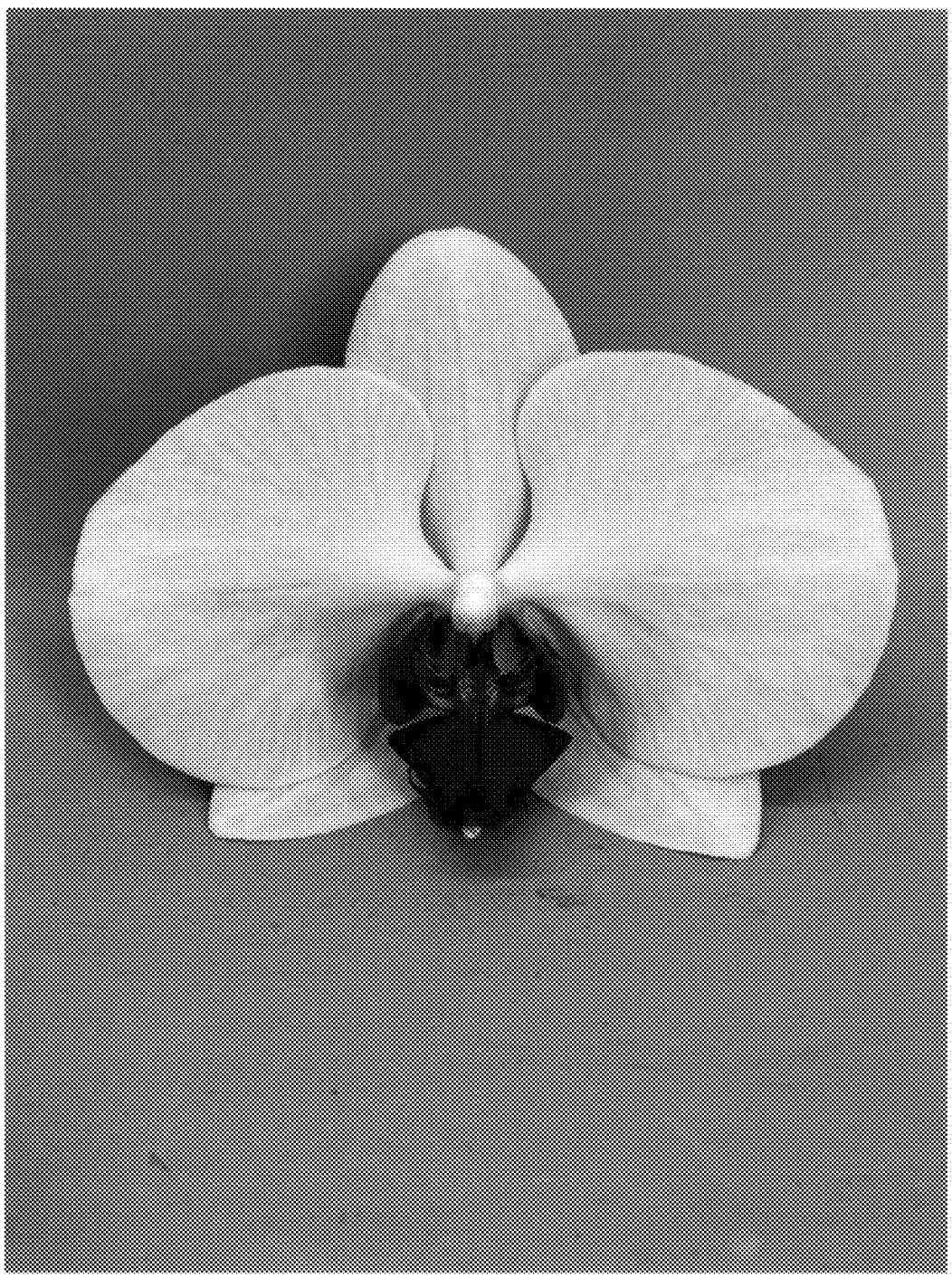
FIG. 2 shows a close-up of a flower of 'PHA474649'.
Figure 3:
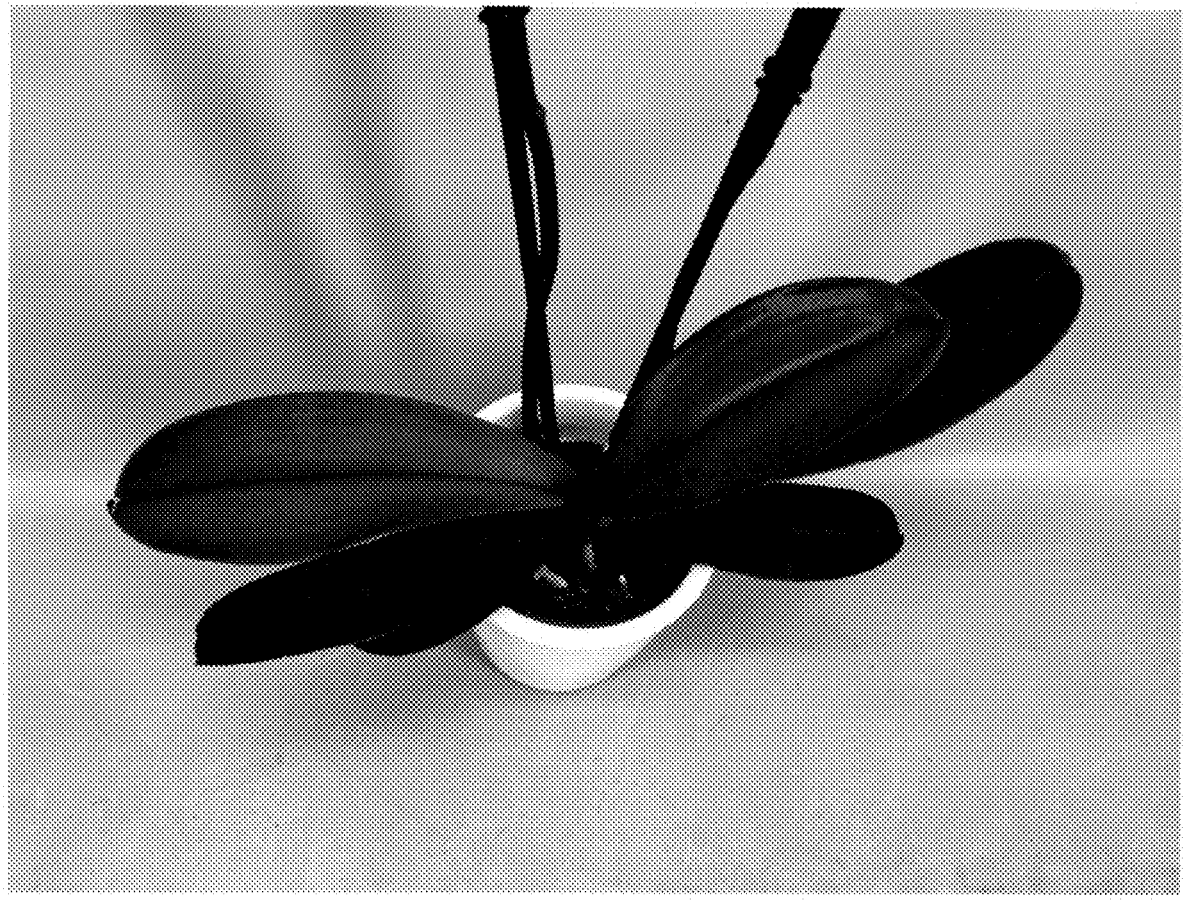
FIG. 3 shows an overhead, close-up view of the leaves of 'PHA474649'.

The following detailed description sets forth the distinctive characteristics of 'PHA474649'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is the R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHA474649'.

Parentage:

*Female parent.*—*Phalaenopsis* cultivar '13-57810-02' (unpatented).

*Male parent.*—*Phalaenopsis* cultivar '14-65219-03' (unpatented).

Propagation:

*Type.*—Meristem tissue culture.

Roots:

*Root description.*—Greyed-green colored roots (a color in between RHS 190B and RHS 190C) with branching lateral roots having purplish-red (RHS N77B) and greenish-yellow colored root tips (RHS 151B).

Plant:

*Crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme inflorescence.

*Height* (*from soil level to top of inflorescence*).—Approximately 65.0 cm to 75.0 cm.

*Width* (*measured from leaf tips*).—About 38.0 cm to 40.0 cm.

*Vigor.*—Strong.

Leaves:

*Mature leaves.*—Quantity per plant: 6 to 8 leaves are produced before flowering. Length (fully expanded): 20.0 cm to 23.0 cm. Width: 7.0 cm to 8.0 cm. Position of the broadest part of the leaf: At the middle. Shape: Obovate. Base shape: Moderately elongated. Apex: Obtuse slightly asymmetric. Leaf blade angle with the petiole (measured from the horizontal position): Between 20 degrees and 35 degrees. Leaf margin: Entire. Color: Upper surface: Green (RHS 147A) with dark red margin (RHS 187A). Lower surface: Green (RHS 146A) and dark red towards margins (RHS N186C). Texture (both upper and lower surfaces): Smooth. Thickness: 2.0 mm to 3.0 mm. Variegation: Absent. Venation: Pattern: Parallel. Color of the midvein: Upper surface: Brown (RHS 200A). Lower surface: Brown (RHS 200B).

Peduncle:

*Quantity per plant.*—2.

*Number of flowers per peduncle.*—10 to 15.

*Length.*—65.0 cm to 75.0 cm.

*Diameter.*—5.0 mm to 7.0 mm.

*Strength.*—Strong.

*Aspect.*—Upright to slightly pendent.

*Texture.*—Smooth.

*Color.*—Brown (RHS 200A) with a gentle touch of green (RHS 146D).

*Internode length.*—4.5 cm to 5.5 cm.

Inflorescence description:

*Appearance.*—Upright to slightly pendent, raceme inflorescence with bilaterally symmetrical flowers that open in succession beginning with the lowermost flower.

*Number of inflorescences.*—2.

*Inflorescence size.*—Height (from base to tip): 250.0 mm to 400.0 mm.

*Flowering time.*—First flowers can be expected 10 to 11 months after planting in a 12-cm pot.

*Flower.*—Height: 80.0 mm to 85.0 mm. Diameter: 95.0 mm to 100.0 mm. Depth of lip: 23.0 mm to 25.0 mm.

*Flower shape.*—Flat.

*Flower longevity.*—On the plant: 11 to 13 weeks.

*Fragrance.*—Absent.

*Flower bud.*—Average size: Large. Length: 22.0 mm to 24.0 mm. Width: 19.0 mm to 21.0 mm. Shape: Egg shaped. Color: Yellow-green (a color in between RHS N144A and RHS 150C) with a gentle touch of light purple (RHS N75B).

*Petals.*—Arrangement: Open/free. Shape: Moderately compressed. Apex: Slightly emarginated asymmetric. Margin: Entire. Length (from base to tip): 44.0 mm to 46.0 mm. Width: 55.0 mm to 57.0 mm. Position of the broadest part of the petal: Toward the base. Color (when fully opened): Upper surface: Basic color: Light greenish-yellow (RHS 4C). Over color: Touch of white (RHS NN155C) and very light purple (RHS 76B) at the base and light purple diluting stripes (RHS N75C) toward margins. Lower surface: Basic color: Light greenish-yellow (RHS 2D). Over color: Touch of very light purple (RHS 76D) at the base; very light purple midvein (RHS 76B). Number of spots, dots, and stripes on the petals (upper surface): Medium stripes. Color of spots, dots, and stripes on the petals (upper surface): RHS N75C. Density of netting of the petals (upper surface): None. Color of the netting (upper surface): Not applicable.

*Dorsal sepal.*—Shape: Elliptic. Apex: Emarginated symmetric. Margin: Entire. Length (from base to tip): 46.0 mm to 48.0 mm. Width: 34.0 mm to 36.0 mm. Position of the broadest part of the dorsal sepals: At the middle. Color (when fully opened): Upper surface: Basic color: Light greenish-yellow (RHS 4C). Over color: Touch of white (RHS 155C) at the base; few diluting light purple stripes (RHS N75D). Lower surface: Basic color: Light greenish-yellow (RHS 2D). Over color: Light yellow-green (RHS 145C); touch of light purple (RHS N75C) toward the tips. Number of spots, dots, and stripes on the dorsal sepals (upper surface): Few stripes. Color of spots, dots, and stripes on the dorsal sepals (upper surface): RHS N75D. Density of netting of the dorsal sepals (upper surface): None. Color of the netting (upper surface): Not applicable.

*Lateral sepals.*—Shape: Ovate. Apex: Obtuse asymmetric. Margin: Entire. Length (from base to tip): 45.0 mm to 47.0 mm. Width: 32.0 mm to 34.0 mm. Position of the broadest part of the lateral sepals: Toward the base. Color (when fully opened): Upper surface: Basic color: Light greenish-yellow (RHS 4C). Over color: Touch of light yellow-green (RHS 145C) and dotted RHS 185C at the base. Lower surface: Basic color: Light yellow-green (RHS 150D). Over color: Light yellow-green (RHS 145C) with a touch of dark purplish-pink (RHS 186C) at the base; dark purplish-pink midvein (RHS 186C) toward the tip. Number of spots, dots, and stripes on the lateral sepals (upper surface): Few stripes and many spots at the base. Color of spots, dots, and stripes on the lateral sepals (upper surface): Stripes and spots RHS 185C. Density of netting of the lateral sepals (upper surface): None. Color of the netting (upper surface): Not applicable.

*Labellum* (*lip*).—Whiskers: Present. Length of whiskers: 11.0 mm to 13.0 mm. Color of whiskers: Purplish-red (RHS 60C) at the base; red toward tips (RHS 183C); light yellow tips (RHS 162C). Pubescence on the lip: Absent.

*Lateral lobe.*—Shape: Type V (as described in the International Union for the Protection of New Varieties of Plants (UPOV) Test Guidelines for *Phalaenopsis*); spatulate Margin: Moderately undulated. Length: 18.0 mm to 20.0 mm. Width: 15.0 mm to 17.0 mm. Color: Upper surface: Light yellow-green (RHS 4D) with a touch of yellow (RHS 12A) with red stripes (RHS 184B) at the base; red (RHS 185A) toward margin on one side with a touch of orange (RHS 170A) and reddish-purple (RHS N78B) toward the tip. Lower surface: White (RHS NN155C); reddish-purple stripes (RHS N78B) at the middle; red (RHS 185A) at the base toward margin on one side with a touch of orange (RHS 170B); light purple-pink (a mix of RHS N78C and RHS 76A) toward tip. Number of spots and stripes on the lateral lobe: Medium stripes. Color of spots and stripes on the lateral lobe: RHS 184B. Density of netting of the lateral lobe: None. Color of the netting: Not applicable.

*Apical lobe.*—Shape: Triangular. Margin: Entire. Length: 21.0 mm to 23.0 mm. Width: 23.0 mm to 25.0 mm. Color: Upper surface: Dark red margin (RHS 183B) and a touch of yellow (RHS 7B) at the base; red wings (RHS 60A); purplish-red toward whiskers (RHS 60C). Lower surface: White (RHS NN155C) at the middle from base toward whiskers; purplish-pink (RHS N78C) toward margins; mix of yellow (RHS 13C) and purplish-red (RHS 59B) toward wings; purplish-red (RHS 59B) toward wings; purplish-pink (RHS N78C) toward margins. Number of spots and stripes on the apical lobe: None. Color of spots and stripes on the apical lobe: No.t applicable. Density of netting of the apical lobe: None. Color of the netting: Not applicable. Bump and ridge: Absent.

*Callus.*—Average size: Small. Height: 6.0 mm to 7.0 mm. Length: 5.0 mm to 6.0 mm. Width: 4.0 mm to 5.0 mm. Color: Light yellow-green (RHS 4D) and yellow (RHS 7B) toward tips; dotted RHS 183C.

Reproductive organs:

*Column.*—Length: 7.0 mm to 8.0 mm. Diameter: 4.0 mm to 5.0 mm. Color: White (RHS NN155C).

*Pollinia.*—Quantity: 2. Diameter: 0.8 mm to 1.0 mm. Color: Orange-yellow (RHS 23A).

*Ovary.*—Length: 13.0 mm to 15.0 mm. Diameter: 2.1 mm to 2.5 mm.

*Pedicel.*—Length: 40.0 mm to 42.0 mm. Diameter: 2.6 mm to 2.9 mm. Color: Light yellow-green (RHS 145C); lighter yellow-green (RHS 145D) with a touch of light purple (RHS N75B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA474649' differs from the female parent plant '13-57810-02' (unpatented) in that 'PHA474649' has wider flowers and moderately compressed petals, whereas '13-57810-02' has more narrow flowers and medium petals.

'PHA474649' differs from the male parent plant '14-65219-03' (unpatented) in that 'PHA474649' has moderately asymmetric symmetry of the leaf apex and emarginated petal apex, whereas '14-65219-03' has symmetric or slightly asymmetric symmetry of the leaf apex and rounded petal apex.

'PHA474649' is most similar to the commercial *Phalaenopsis* plants named 'PHALHOCH' (U.S. Plant Pat. No. 32,595) and 'PHALEKDEK' (U.S. Plant Pat. No. 32,024). 'PHA474649' differs from the commercial variety 'PHALHOCH' in that 'PHA474649' has short whiskers, triangular apical lobes, and raceme inflorescence, whereas 'PHALHOCH' has very short whiskers, elliptical apical lobes, and panicle inflorescence. Further, the mature leaf width of 'PHA474649' is much wider than 'PHALHOCH'.

'PHA474649' differs from the commercial variety 'PHALEKDEK' in that 'PHA474649' has moderately asymmetric symmetry of leaf apex, semi-erect leaf attitude, and emarginated petal apex, whereas 'PHALEKDEK' has strongly asymmetric symmetry of leaf apex, erect to semi-erect leaf attitude, and obtuse petal apex.

I claim:

1. A new and distinct variety of *Phalaenopsis* plant named 'PHA474649', substantially as described and illustrated herein.

* * * * *